United States Patent
Singh et al.

(10) Patent No.: US 7,527,814 B2
(45) Date of Patent: May 5, 2009

(54) PROCESS FOR THE ISOLATION OF CALLITERPENONE

(75) Inventors: Anil Kumar Singh, Lucknow (IN); Suman Preet Singh Khanuja, Lucknow (IN); Sudeep Tandon, Lucknow (IN); Alok Kalra, Lucknow (IN); Deeptanjali Sahoo, Lucknow (IN); Atul Prakash Kahol, Lucknow (IN); Madan Mohan Gupta, Lucknow (IN); Ram Kishor Verma, Lucknow (IN); Arun Kumar Kukreja, Lucknow (IN); Mansoor Alam, Lucknow (IN); Guru Das Bagachi, Lucknow (IN); Ravi Prakash Bansal, Lucknow (IN); Mahendra Pandurang Darokar, Lucknow (IN); Anil Kumar Gupta, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/699,764

(22) Filed: Jan. 30, 2007

(65) Prior Publication Data

US 2007/0225168 A1    Sep. 27, 2007

(30) Foreign Application Priority Data

Mar. 22, 2006  (IN) .................. 0775/DEL/2006

(51) Int. Cl.
*A61K 36/00*    (2006.01)

(52) U.S. Cl. ...................... 424/774; 424/725
(58) Field of Classification Search ............ None
See application file for complete search history.

(56) References Cited

U.S. PATENT DOCUMENTS 6,673,749 B1    1/2004   Singh et al.

OTHER PUBLICATIONS

Chatterjee et al. (Tetrahedron (1972), vol. 28, pp. 4319-4323).*
Subramanian et al. (Phytochemistry (1974), vol. 13, pp. 306-307).*
Singh et al. (Phytochemistry (1994), vol. 37, No. 2, pp. 587-588).*
Agrawal et al. *Indian J. Chem.* 1996 (35B), 803-805.
Ahamad and Zaman *Tetrahedron Lett.*, 1973, 2179.
Chatterjee, A. et al. *Tetrahedron* 1972, 28, 4319-4323.
Fujita et al. *Phytochemistry*, 1975 (14) 2249.
Gui Liu et al. *Helvetica Chemica Acta* 2003, (86) 420-437.
Sen Gupta et al. *Journal of Indian Chemical Society*, 1976 (LIII), 218-219.
Singh et al. *Indian J. of Chem.*, 1994 (33b), 1205.
Singh et al. *Phytochemistry* 1994, 37(2), 587-588.
Subramaniam et al. *Phytochemistry*, 1974 (13), 306-307.
Wong et al. *Acta Crystallography, Section C* 1991 (47), 906.

* cited by examiner

*Primary Examiner*—Susan C Hoffman
(74) *Attorney, Agent, or Firm*—Brinks Hofer Gilson & Lione

(57) ABSTRACT

The invention provides a simple method for isolation of calliterpenone (16α,17 dihydroxy-3-oxo phyllocladane), a phyllocladane diterpenoid with the plant growth regulating properties, from plant genus *Callicarpa*.

20 Claims, No Drawings

PROCESS FOR THE ISOLATION OF CALLITERPENONE

RELATED APPLICATIONS

This application claims priority under 35 U.S.C. §119 to Indian patent application Serial No. 0775/DEL/2006, filed Mar. 22, 2006. The disclosure of this priority application is incorporated herein in its entirety.

FIELD OF THE INVENTION

The present invention relates to a process for the isolation of a plant extract. More particularly, the invention relates to an improved process for the isolation of calliterpenone ($16\alpha,17$ dihydroxy-3-oxo phyllocladane), a plant growth promoting phyllocladane diterpenoid.

BACKGROUND OF THE INVENTION

Recently phyllocladane diterpenoids isolated from plant *Callicarpa macrophylla* Vahl (Family Verbenaceae) have been found to promote plant growth and alleviate the effects of growth retardant allelochemicals. (Singh et al., U.S. Pat. No. 6,673,749 (2004)) These novel activities pave the utility of these compounds as natural plant growth promoters and for alleviation of the growth retarding effects produced by allelochemicals. The plant growth promoters hold commercial importance in intensive agriculture and have become most attractive in the agro-business of high value crops for organic cultivation. Gibberellins (specially $GA_3$) are the most important group among the known plant growth regulators (auxins, cytokinins, abscisic acid, gibberellins, and ethylene, etc.) used for enhancing the productivity of commercial crops. However, the high cost restricts its application to high value crops only. Among, the phyllocladane diterpenoids from *Callicarpa macrophylla* viz. calliterpenone ($16\alpha,17$ dihydroxy-3-oxo phyllocladane) and its four derivatives (calliterpenone monoacetate, calliterpenone diacetate, iso-propylidinocalliterpenone and trihydroxy calliterpenone), the most promising effects on growth promotion of roots, shoots and seed germination were demonstrated by calliterpenone (U.S. Pat. No. 6,673,749). Thus, the economical isolation of calliterpenone is needed for commercial exploitation in agro-business.

Calliterpenone and its monoacetate were first isolated by Chaterjee et al. (Tetrahedron, (28), 4319 (1972)) from the dry powdered stem and leaves of *Callicarpa macrophylla*. In that method, 8 kg of dried powdered leaves were extracted for 30 hours in hexane to produce a residue (1.5 g), which on column chromatography yielded 0.01% and 0.008% calliterpenone and its monoacetate, respectively. Subramaniam et al. (*Phytochemistry*, (13), 306-307 (1974)) isolated calliterpenone from the chloroform extract of dried leaves by column chromatography (yield not reported). Sen Gupta et al. (*Journal of Indian Chemical Society*, (LIII), 218-219 (1976)) isolated calliterpenone by column chromatography of neutral fractions of rectified sprit extract (yield not reported).

In all the above reports, the isolation of calliterpenone and its monoacetate have involved extraction of plant material in various solvents followed by column chromatography. Previously from this institute, Singh & Agarwal (*Phytochemistry*, 37(2), 587-588 (1994) and *Indian J. of Chem.*, (33b), 1205 (1994)) isolated calliterpenone and its monoacetate by column chromatography of deposits (14 g) obtained in water extract of fresh leaves (50 kg) yielding 0.011% and 0.006% of calliterpenone and its monoacetate, respectively. The structural studies of calliterpenone and other phyllocladane diterpenoids have been done in detail by Ahamad and Zaman (*Tetrahedron Lett.*, 2179 (1973)), Fujita et al. (*Phytochemistry*, (14) 2249 (1975)), Wong et al. (*Acta Crystallography, Section C* (47), 906 (1991)), Agrawal et al. (*Indian J. Chem.* (35B), 803-805 (1996)) and Gui Liu et al. (*Helvetica Chemica Acta*, (86) 420-437 (2003)). The yield of calliterpenone in all the reports described so far was about 0.01% on dry wt. basis (Chaterjee et al., 1972) or on fresh wt. basis (Singh et al., 1994).

For economical isolation of calliterpenone, extraction of plant material by various organic solvents produces dark viscous residues having total extractable constituents from which isolation of calliterpenone by column chromatography produced very low yield of calliterpenone. Therefore, efforts were made to isolate calliterpenone from the water extract of plant *Callicarpa macrophylla* using simple methods and avoiding column chromatography. Accordingly, there is a need for improved methods for isolating calliterpenone providing higher yields.

SUMMARY OF THE INVENTION

A simple method is provided for isolation of calliterpenone ($16\alpha,17$ dihydroxy-3-oxo phyllocladane), a phyllocladane diterpenoid with the plant growth regulating properties, from plant genus *Callicarpa*, wherein the recovery of calliterpenone has been increased (40 to 92 fold compared to the previous methods). One embodiment of the present invention comprises boiling of water washed plant material for two to four hours in pure water or 1-5% alkaline water, concentrating the extract to half the volume under vacuum, partitioning of the concentrate with water immiscible organic solvent at a temperature ranging from 20-40° C., hydrolyzing the solvent fraction with 4-10% alkali if pure water is used in first extraction step, and purifying the residue by filtration through celite using a mixture of polar and nonpolar solvents.

The development of this process technology will pave the way for commercial utilization of calliterpenone as a plant growth promoter. Calliterpenone produces a better plant growth promoting effect than $GA_3$ if used in a particular method and also antagonizes the growth retardant effects produced by allelochemicals.

DETAILED DESCRIPTION OF THE INVENTION

Accordingly, the present invention provides an improved process for the isolation of calliterpenone ($16\alpha,17$ dihydroxy-3-oxo phyllocladane) from plant genus *Callicarpa*. As used herein, calliterpenone refers to $16\alpha,17$ dihydroxy-3-oxo phyllocladane.

In one embodiment of the present invention, the process comprises the steps of: a) drying the leaves of *Callicarpa macrophylla* followed by grinding to make a fine powder; b) heating the powder obtained from step (a) with water for 2-3 hours with constant stirring to form a water extract; c) optionally heating the powder obtained from step (a) with 1-5% alkali solution for 2-3 hours with constant stirring to form a water extract; d) concentrating the water extract obtained from step (b) or step (c) to half the volume; e) further extracting the solution obtained from step (d) with a water immiscible organic solvent at temperature ranging from 20 to 40° C. and repeating 4-5 times; f) pooling the extracts obtained from step (e); g) optionally hydrolyzing the extract obtained from step (f) with 4-10% alkaline methanol or ethanol for two to three hours; and h) drying and purifying the desired product.

In another embodiment of the present invention, the alkaline water is prepared by dissolving 1 to 5% alkali selected from the group consisting of sodium or potassium hydroxide in water. Further, in another embodiment of the present invention, the water immiscible solvents are selected from the group consisting of hydrocarbons such as pentane, hexane, benzene; ethers such as diethyl ether, methyl ethyl ether; chlorinated solvents such as dichloromethane, chloroform; or alcohols like butanol, etc.

In yet another embodiment of the present invention, dichloromethane is used for further extracting the water extract to increase the yield of the calliterpenone.

In still another embodiment of the present invention, the purification is carried out by absorbing the product over celite followed by washing with 20% ethyl acetate in hexane and further washing with ethyl acetate and hexane in the ratio 1:1 and drying the filtrate under vacuum followed by crystallization.

The present invention provides a process for isolation of calliterpenone (16α,17 dihydroxy-3-oxo phyllocladane), a phyllocladane diterpenoid with the plant growth regulating properties from plant *Callicarpa macrophylla* Vahl (Family Verbenaceae). Besides growth promoting activities, calliterpenone also antagonizes the growth retardant effects produced by allelochemicals (Singh et al., U.S. Pat. No. 6,673, 749 (2004)). The economical isolation of calliterpenone is needed for commercial exploitation of this compound in agro-business. Experiments were carried out for the isolation of calliterpenone and are explained in the following examples.

All the organic solvents viz hexane, benzene, ethyl ether, ethyl acetate, chloroform, methanol and ethanol, etc., can extract calliterpenone from the plant, but a number of other compounds and chlorophyll are also extracted in all these extracts. The process of isolation of pure calliterpenone from these extracts is very tedious, time and labor consuming by utilizing column chromatography, and problematic for removal of the chlorophyll. To avoid chlorophyll, the plant materials were extracted in water as described by Singh et al. (1994). To make the process easier and maximize the yield of calliterpenone, many experiments were carried out as described in following examples.

The following examples are given by way of illustration of the present invention and should not be construed to limit the scope of present invention.

EXAMPLE 1

Plant material was collected during January 2004 from its natural habitat from the nearby area of CIMAP Resource Center Pantnagar situated in lower Himalayan region (Uttranchal, India). The leaves were separated from twigs and dried in shade and powdered using a mixer grinder. Dried intact leaves (300 g) were extracted using a 10 L capacity Clevenger's type glass apparatus with 3 L of water to remove the steam volatile part. The decoction thus produced was filtered and concentrated to half of its volume and extracted repeatedly with hexane (4×500 mL) using a separating funnel. The hexane extract on concentration was found to have both calliterpenone and its monoacetate as visualized by TLC. The marc was again extracted with chloroform (4×500 mL). The chloroform extract was also found to have similar TLC pattern as compared to the hexane extract. All the extracts were mixed and concentrated using a rotary film evaporator to produce 1.52 g of a dark brown colored residue. The residue showed presence of 44.8% calliterpenone in the mixture (estimation was done using HPLC as described in Example 8). On TLC (1:3 hexane:ethyl acetate and iodine chamber), the extract showed the presence of five major compounds. Two were identified as calliterpenone and calliterpenone monoacetate. Three other compounds were present along with many impurities present at the top of the TLC plates. Pure calliterpenone was obtained by absorbing the residue over silica gel and eluting with 1 L hexane and hexane:ethyl acetate with increasing polarity, first with 10% ethyl acetate in hexane then with 20%, 30% and lastly with 50%. The last eluent fractions on further purification by rechromatography gave pure calliterpenone, 0.34 g (0.11% yield). The conformity of calliterpenone was done with an authentic sample obtained from our previous studies (Singh & Agarwal, *Phytochemistry*, 37(2), 587-588 (1994) and *Indian J. of Chem.*, (33b) 1205 (1994)).

EXAMPLE 2

To increase the amount of calliterpenone, the monoacetate present in the extract was hydrolyzed as follows:

Dry powdered leaf (1 kg) was extracted with water (2×5 L), and the total water extract was extracted with chloroform in a liquid-liquid extractor. The extract was concentrated using a rotary film evaporator producing (11.72 g) of a dark greenish black oily and sticky residue. The residue was taken up in chloroform (150 mL) and filtered through activated charcoal. The resulting solution was successively washed with 5% sodium bicarbonate (3×50 mL), then 5% sodium carbonate to afford the neutral fraction. The $CHCl_3$ extract was dried under reduced pressure, and then taken up in methanol (100 mL). The methanol extract was refluxed with 5% NaOH in water for one hour, cooled, filtered and extracted in $CHCl_3$ washed several times to remove alkali. The chloroform extract was concentrated. The residue washed with cold ether to remove yellow color, producing a yellow white amorphous compound (0.89 g) having calliterpenone as the major constituent with 3 more impurities (yield: 0.089% dry leaves wt. basis). To purify the compound, it was filtered through celite by absorbing over 2 g celite and making a bed with 20 g celite and washing first with 500 mL 10% ethyl acetate in hexane then with 50% ethyl acetate in hexane. The 50% ethyl acetate: hexane washings on concentration in a rotary film evaporator produced a white amorphous powder of 407 mg of pure calliterpenone (yield: 0.040% dry wt. basis). The purity of the compound was 79% as estimated by HPLC as described in Example 8.

The above experiment has the following limitations. (1) In the above method, chloroform was used many times for extraction, and at each extraction some emulsions formed in which loss of compound was very much evident. (2) The use of activated charcoal may be avoided as the color of the solution obtained after the treatment did not change and compound loss occurred. (3) During hydrolysis, aqueous alkali was used. The presence of water at this stage was helpful in precipitation of the saponified materials, but during extraction with $CHCl_3$ many impurities also were extracted.

EXAMPLE 3

To avoid these limitations the experiment was repeated as below.

Fresh plant material was collected in July 2004 when the plants were in their vegetative stage, and no flowering and fruiting was observed during this period. Semidried leaves (300 g) having (12% moisture) were washed to remove all the dirt and were extracted two times in water using a 10 L capacity Clevenger type glass apparatus (2×6 L). The total extract (about 12 L) was concentrated to 3 L under vacuum and extracted in chloroform (5×300 mL) using a separating funnel. All the extracts were pooled and concentrated, the residue (7.02 g) thus obtained was dissolved in methanol (100 mL) and hydrolyzed with 7% methanolic NaOH (10 mL) by refluxing on a water bath for three hours (hydrolysis of monoacetate was monitored by TLC). To the hydrolyzed solution, water (250 mL) was added. A precipitate appeared which was allowed to settle down for 1 h, and then filtered through a Whatman No. 1 filter paper. The filtrate was extracted with $CHCl_3$. The $CHCl_3$ extract washed until neutral and concentrated. The residue obtained washed 2-3 times with ethyl ether and was purified as described in the previous experiment Example 2 to yield 2.4 g of calliterpenone (0.92% yield) having 86% purity (estimated as described in Example 8).

EXAMPLE 4

For further simplification of the experiment and to enhance the percentage of calliterpenone in the extract, the calliterpenone monoacetate present in the extract was hydrolyzed using 10% NaOH as follows.

Dried powdered leaves (50 g) were boiled in water (500 mL) using a reflux condenser. The resulting water extract was made alkaline by adding 10% NaOH (5-7 mL) heated on a water bath for 30 min. with constant stirring. This solution was cooled and extracted in chloroform (4×100 mL). The combined extracts were mixed, concentrated, and dried over anhydrous sodium sulphate. The chloroform extracts were concentrated to dryness, cooled and washed with solvent ether (3 times) whereby all the colored compounds were extracted in ether by slow washing. Almost pure calliterpenone was observed with slight impurities at the top of the TLC plate. A total of 0.05 g was recovered (0.1% yield). Conversion of monoacetate was complete, but the yield was very low as compared to previous experiment.

EXAMPLE 5

The experiment was further modified as follows.

Based upon the observation from Example 3 that semidried leaves produced better recovery of calliterpenone, dried leaves were soaked with water before processing as follows:

Dried leaves (200 g) were cleaned with water and dipped for two hours before extraction in Clevenger type glass apparatus with 6 L of water for three hours. The water extract was concentrated to 2.5 L under vacuum. The extract was further extracted four times with dichloromethane (250 mL) in a separating funnel. All the extracts were pooled together and dried under vacuum to yield 2.3 g of residue. The dichloromethane extracted water extract was further partitioned in chloroform (4×250 mL), which on concentration gave a green residue which was devoid of calliterpenone and calliterpenone monoacetate showing that all these compounds had been extracted with dichloromethane. The residue obtained from dichloromethane extract was taken up in methanol and purified as described in Example 3 to yield calliterpenone (0.49% yield) with 86% purity (estimated as described in Example 8). The yield of calliterpenone is less than that of Example 2. The reason may be that the desired compound is more easily extractable from fresh plant material than from the dried material. It is important to note that calliterpenone and its acetate are not soluble in water as such, but are extractable in water from the plant due to presence of certain other constituents. It is also evident that when dried grinded plant material was used it produced dark green black residue, which was oily in nature (Example 2) and produced a much lesser amount of calliterpenone (0.04%) on processing. When the leaves were not ground and dipped in water before extraction, the yield increased as in the present experiment (0.49%).

EXAMPLE 6

To study the feasibility of the process for recovery of calliterpenone, a larger batch of dried leaves (15 kg, collected during September 2004) were processed as follows:

Dried leaves were extracted for two hours in water (70 L) using a 100 L capacity stainless steel jacketed extraction unit with steam heating. The extract was concentrated in a vacuum concentrator to about 20 L. The concentrated water extract was partitioned with chloroform using a liquid-liquid extractor, and the residue obtained in the chloroform extract was hydrolyzed with 10% methanolic sodium hydroxide. The solvents was removed from the hydrolyzed solution using a rotary film evaporator, and the residue thus obtained washed with water until the color was removed. The residue was dried in a vacuum dryer, and finally purified by filtration through celite to afford 22.6 g calliterpenone (0.13% yield). The yield was low as compared to previous examples. This may be due to time of collection of plant material.

EXAMPLE 7

To further simplify the extraction the experiment was modified as follows.

Dried leaves (200 g) were cleaned and dipped in water for two hours. The leaves were extracted in a Clevenger type glass apparatus along with 6 L of 1% alkaline water (60 g sodium hydroxide dissolved in 6 L water) for three hours, and the water extract thus obtained was concentrated to half its volume and extracted with dichloromethane (4×200 mL). The dichloromethane extract was further processed as described in Example 3 to afford calliterpenone (0.46% yield) with 84% purity (estimated as described in Example 8).

The fact that the yield of calliterpenone in both Examples 5 and 7 is almost the same implies that hydrolysis of calliterpenone monoacetate in the plant material or after the extraction produces similar amounts of calliterpenone. Since the processing in Example 6 is simple and reduces one step, it is better for commercial purpose.

This process is very simple and can be utilized commercially with semidried plant material.

EXAMPLE 8

The difference recorded in yield of calliterpenone in all the above examples may be due to time of collection of plant material and the variations in the steps involved. To ascertain the content of calliterpenone present in plant, it was estimated in the leaves of different collections.

Dried powdered leaves (25 g) of each of the January, July, and September collections were extracted in 200 mL of 2% alkaline water (4 g NaOH in 200 mL water) for two hours, and the extracts partitioned with dichloromethane.

The dichloromethane extracts were dried and dissolved in methanol. Calliterpenone was estimated using HPLC on a Shimadzu LC-10A gradient analytical HPLC equipment using acetonitrile:water (45:55) mobile phase, detection at 220 nm, and a Waters Spherisorb ODS-2 column, 10 μm, 250×4.6 mm I.D. The calliterpenone content was found to be 0.27%, 1.03% and 0.15% in leaves collected during January, July, and September, respectively, while the fruits have 0.28%. No calliterpenone was detected in the stems.

Advantages

In the process of the present invention, advantages include:

Extraction with pure water or with alkaline water minimizes extraction of the undesirable constituents. Extraction with alkaline water, besides hydrolyzing the calliterpenone monoacetate present, also hydrolyzes esters and neutralizes the free acids present in the plant material, and thus makes the process very simple for producing 40 to 92 folds enhancement in yield of calliterpenone.

Extraction and hydrolysis of the monoacetate simultaneously enables the extraction of the total calliterpenone present in the plant either in the free form or in the acetate form.

Extraction of plant material with alkaline water reduces the processing cost as compared to extraction with solvents.

Column chromatography is not necessary which saves time and money and makes the process very simple and commercially feasible.

The above examples are illustrative only, and should not be interpreted as limiting since further modifications of the disclosed embodiments will be apparent to those skilled in the art in view of this teaching. All such modifications are deemed to be within the scope of the embodiments disclosed herein.

We claim:

1. A process for the isolation of calliterpenone from plant genus *Callicarpa*, the process comprising the steps of:
   a. drying leaves of *Callicarpa macrophylla*;
   b. grinding dry leaves of *Callicarpa macrophylla* to make a powder;
   c. heating the powder with an aqueous solution to obtain an aqueous extract; wherein the aqueous solution comprises between about 1 and about 5 wt % alkali;
   d. concentrating the aqueous extract to form a concentrated extract wherein a volume of the concentrated extract is less than a volume of the aqueous extract;
   e. extracting the concentrated extract with a water immiscible organic solvent at a temperature to form an organic extract; wherein the water immiscible organic solvent is selected from the group consisting of pentane, hexane, diethyl ether, ethyl ether, dichloromethane and butanol;
   f. concentrating the organic extract to form crude calliterpenone; and
   g. purifying the crude calliterpenone to form calliterpenone.

2. The process of claim 1, wherein the volume of the concentrated extract is about half the volume of the aqueous extract.

3. The process of claim 1, wherein step (e) is done at a temperature between about 20 to 40° C.

4. The process of claim 3, wherein step (e) is repeated at least 4 times; and further comprising combining the organic extracts.

5. The process of claim 1, wherein the heating is done for about 2 to about 3 hours with constant stirring;
   wherein the volume of the concentrated extract is about half the volume of the aqueous extract;
   wherein step (e) is done at a temperature between about 20 and about 40° C.;
   wherein step (e) is repeated at least 4 times;
   further comprising combining the organic extract with an alkaline alcohol solution about 4 to about 10 wt % alkali, wherein the alcohol is methanol or ethanol; and
   drying the organic extract.

6. The process of claim 5, wherein the alkali is sodium hydroxide or potassium hydroxide.

7. The process of claim 5, wherein the water immiscible solvent is dichloromethane.

8. The process of claim 5, wherein the purifying comprises:
   absorbing the crude calliterpenone over celite;
   washing the celite with about 20% by volume ethyl acetate hexane to form a first wash extract;
   washing the celite with 1:1 by volume ethyl acetate and hexane to form a second wash extract;
   combining and concentrating the first and second wash extract; and
   crystallizing the calliterpenone.

9. The process of claim 1, wherein the alkali is sodium hydroxide or potassium hydroxide.

10. The process of claim 1, wherein the water immiscible solvent is dichloromethane.

11. The process of claim 1, wherein the purifying comprises:
    absorbing the crude calliterpenone over celite;
    washing the celite with about 20% by volume ethyl acetate in hexane to form a first wash extract;
    washing the celite with 1:1 by volume ethyl acetate and hexane to form a second wash extract;
    combining and concentrating the first and second wash extract; and
    crystallizing the calliterpenone.

12. A process for the isolation of calliterpenone from plant genus *Callicarpa*, the process comprising the steps of:
    a. drying leaves of *Callicarpa macrophylla*;
    b. grinding dry leaves of *Callicarpa macrophylla* to make a powder;
    c. heating the powder with an aqueous solution to obtain an aqueous extract;
    d. concentrating the aqueous extract to form a concentrated extract wherein a volume of the concentrated extract is less than a volume of the aqueous extract;
    e. extracting the concentrated extract with a water immiscible organic solvent at a temperature to form an organic extract; wherein the water immiscible organic solvent is selected from the group consisting of pentane, hexane, diethyl ether, ethyl ether, dichloromethane and butanol;
    f. concentrating the organic extract and hydrolyzing the organic extract with an alkali alcohol solution to form crude calliterpenone;
    purifying the crude calliterpenone to form calliterpenone.

13. The process of claim 12, wherein the alkali alcohol solution comprises about 4 to 10 wt % alkali.

14. The process of claim 13, wherein the alcohol is methanol or ethanol.

15. A process for the isolation of calliterpenone from plant genus *Callicarpa*, the process comprising the steps of:
    a. drying leaves of *Callicarpa macrophylla*;
    b. grinding dry leaves of *Callicarpa macrophylla* to make a powder;
    c. heating the powder with an aqueous solution to obtain an aqueous extract;
    d. concentrating the aqueous extract to form a concentrated extract wherein a volume of the concentrated extract is less than a volume of the aqueous extract;
    e. extracting the concentrated extract with a water immiscible organic solvent at a temperature to form an organic extract; wherein the organic solvent is selected from the group consisting of pentane, hexane, diethyl ether, ethyl ether, dichloromethane and butanol;
    f. concentrating the organic extract to form crude calliterpenone; and
    g. purifying the crude calliterpenone to form calliterpenone.

16. The method of claim 15, wherein the volume of the concentrated extract is about half the volume of the aqueous extract.

17. The process of claim 15, wherein step (e) is done at a temperature between about 20 to 40° C.

18. The process of claim 17, wherein step (e) is repeated at least 4 times; and further comprising combining the organic extracts.

19. The process of clam 15, wherein the water immiscible solvent is dichloromethane.

20. The process of claim 15, wherein the purifying comprises:
   absorbing the crude calliterpenone over celite;
   washing the celite with about 20% by volume ethyl acetate in hexane to form a first wash extract;
   washing the celite with 1:1 by volume ethyl acetate and hexane to form a second wash extract;
   combining and concentrating the first and second wash extract; and
   crystallizing the calliterpenone.

* * * * *